US012606505B2

(12) United States Patent
Yang et al.

(10) Patent No.: US 12,606,505 B2
(45) Date of Patent: Apr. 21, 2026

(54) METHOD FOR REDUCING RISK OF BURNING AND EXPLOSION IN DEOXYGENATION PROCESS OF OXYGEN-CONTAINING GAS

(71) Applicants:CHINA PETROLEUM & CHEMICAL CORPORATION, Beijing (CN); SINOPEC RESEARCH INSTITUTE OF SAFETY ENGINEERING CO., LTD., Qingdao (CN)

(72) Inventors: Zhe Yang, Qingdao (CN); Jie Jiang, Qingdao (CN); Song Wen, Qingdao (CN); Changsheng Zhang, Qingdao (CN); Wei Xu, Qingdao (CN); Bing Sun, Qingdao (CN); Jinchong Zhao, Qingdao (CN); Yunfeng Zhu, Qingdao (CN); Shoutao Ma, Qingdao (CN); Yuxia Zhang, Qingdao (CN)

(73) Assignees: CHINA PETROLEUM & CHEMICAL CORPORATION, Beijing (CN); SINOPEC RESEARCH INSTITUTE OF SAFETY ENGINEERING CO., LTD., Qingdao (CN)

( * ) Notice: Subject to any disclaimer, the term of this patent is extended or adjusted under 35 U.S.C. 154(b) by 326 days.

(21) Appl. No.: 18/293,679

(22) PCT Filed: May 13, 2022

(86) PCT No.: PCT/CN2022/092715
§ 371 (c)(1),
(2) Date: Jan. 30, 2024

(87) PCT Pub. No.: WO2023/020044
PCT Pub. Date: Feb. 23, 2023

(65) Prior Publication Data
US 2025/0115536 A1     Apr. 10, 2025

(30) Foreign Application Priority Data

Aug. 19, 2021 (CN) .......................... 202110956853.2
Aug. 19, 2021 (CN) .......................... 202110956868.9
Aug. 19, 2021 (CN) .......................... 202110956875.9

(51) Int. Cl.
*C07C 7/148* (2006.01)
*C07C 5/48* (2006.01)

(52) U.S. Cl.
CPC ............ *C07C 7/14858* (2013.01); *C07C 5/48* (2013.01)

(58) Field of Classification Search
None
See application file for complete search history.

(56) References Cited

U.S. PATENT DOCUMENTS

| | | | |
|---|---|---|---|
| 4,299,800 | A | 11/1981 | Nishikawa et al. |
| 2005/0281725 | A1 | 12/2005 | Hague et al. |
| 2014/0316181 | A1 | 10/2014 | Averlant et al. |
| 2015/0203772 | A1 | 7/2015 | Schoch et al. |

FOREIGN PATENT DOCUMENTS

| | | |
|---|---|---|
| CN | 1688675 A | 10/2005 |
| CN | 1955150 A | 5/2007 |

(Continued)

OTHER PUBLICATIONS

Liu, Yingjie et al, "Development of liquid propylene deoxidation catalyst"; Industrial Catalysis, vol. 24, No. 1; Jan. 2016; pp. 61-64.
Miao, Haiyan et al., "Flammability limits of hydrogen-enriched natural gas", International Journal of Hydrogen Energy, Jun. 2011, vol. 36, No. 11, pp. 6937-6947.

*Primary Examiner* — In Suk C Bullock
*Assistant Examiner* — Alyssa L Cepluch
(74) *Attorney, Agent, or Firm* — NKL Law; Allen Xue

(57) ABSTRACT
A method for reducing the risk of burning and explosion in a deoxygenation process of an oxygen-containing gas includes multiple steps. According to this method, in the (Continued)

presence of a gaseous alkane, hydrogen reacts with an oxygen-containing gas from which an unsaturated hydrocarbon has been removed. The oxygen-containing gas contains the oxygen and the unsaturated hydrocarbon, and the content of the oxygen in the oxygen-containing gas is greater than 0.5% by volume. A gaseous alkane is introduced to reduce the risk of burning and explosion of a mixed gas. A hydrocatalytic reaction is carried out to promote oxygen in the mixed gas to react with hydrogen to produce water, which removes oxygen from the oxygen-containing gas and also effectively inhibits carbon deposition on the surface of a catalyst and the production of a carbon oxide, which enhances the toleration for fluctuation of the oxygen content in a raw gas.

17 Claims, 2 Drawing Sheets

(56)                     References Cited

FOREIGN PATENT DOCUMENTS

| | | | |
|---|---|---|---|
| CN | 101142019 | A | 3/2008 |
| CN | 101664679 | A | 3/2010 |
| CN | 102302931 | A | 1/2012 |
| CN | 102433185 | A | 5/2012 |
| CN | 102614934 | A | 8/2012 |
| CN | 104148079 | A | 11/2014 |
| CN | 106566566 | A | 4/2017 |
| CN | 107847859 | A | 3/2018 |
| CN | 110559843 | A | 12/2019 |
| CN | 113244931 | A | 8/2021 |

METHOD FOR REDUCING RISK OF BURNING AND EXPLOSION IN DEOXYGENATION PROCESS OF OXYGEN-CONTAINING GAS

CROSS REFERENCE TO RELATED APPLICATIONS

This application is a U.S. national stage entry of PCT International Application No. PCT/CN2022/092715, filed on May 13, 2022, which claims benefit of the Chinese Patent Applications No. 202110956875.9, 202110956868.9 and 202110956853.2, all filed on Aug. 19, 2021, the contents of which are incorporated herein by reference in its entirety.

TECHNICAL FIELD

The present invention relates to the technical field of purification of mixed gas, specifically relates to a method for reducing the risk of burning and explosion in a deoxygenation process of oxygen-containing gas, in particular to an use of a gaseous alkane in removing oxygen from the oxygen-containing gas.

BACKGROUND ART

The presence of oxygen ($O_2$) in many petroleum refining and chemical production processes is prone to cause adverse effects such as poisoning of catalysts, degradation of product quality and safety accidents. For example, in the reactions using metallic state Ni catalyst, oxygen may result in deactivation of the catalyst due to oxidation; in the olefin polymerization process, oxygen may act as a polymerization inhibitor, affecting the polymerization reaction; the mixing of oxygen into the combustible organic and inorganic gases may trigger combustion or explosion when the amount of oxygen accumulates to a certain concentration, thereby causing the production safety accidents. Therefore, the oxygen in mixed gas of some chemical processes shall be controlled or removed from the perspectives of both the process requirements and production safety. Along with the increasingly stringent requirements on energy-saving, environmental protection and safety production in the refining and chemical industries in China and foreign countries in recent years, there is a growing need for removing oxygen in the industrial mixed gas during the production process, and the control of oxygen content is also increasingly strict. As stipulated in the industrial standard SH 3009-2013 "Design specification for combustible gas discharge system in petrochemical engineering" version 5.3.1, "the combustible gas with oxygen content greater than 2% (vol)" should not be discharged into site-wide combustible gas discharge system, such as flare. The development of chemical process technologies has brought an expanding application scenario of deoxygenation technologies, which also imposes newer and higher requirements on the deoxygenation technologies of mixed gas.

Three deoxygenation methods are mainly used in the industrial production processes at present, namely chemisorptive deoxygenation, high temperature deoxygenation with activated carbon and catalytic deoxygenation. Chemisorptive deoxygenation mainly utilizes a deoxidizing agent (e.g. CN1955150A), which reacts with oxygen and consumes oxygen in the system, thereby fulfill the deoxygenation purpose, such method has defects that the deoxidizing agent has a short service life and cannot be used continuously on a large scale. The high temperature deoxygenation using activated carbon is mainly used for deoxygenation of inert gases and removing oxygen by reacting activated carbon with oxygen under high temperature, but its development is restrained by the disadvantages such as high investment amount, difficult operation, and the temperature cannot be easily controlled. The catalytic deoxygenation serves to remove oxygen by reacting oxygen in the system with hydrogen, carbon monoxide, hydrocarbons and other gases by the action of a catalyst (e.g. LIU Yingjie, et al, "Research and development of liquid propylene deoxygenation catalyst", Industrial Catalysis, 2016, 24(1): 61-64). The process can be applicable to a majority of mixed gas systems and remove most of the oxygen by an efficient catalytic reaction. Meanwhile, it is easy to implement the continuous production, which is conducive to improving the production efficiency and reducing the production costs.

The current catalytic hydrodeoxygenation technology is used for ensuring safety of process and reducing the risk of combustion and explosion of the mixed gas by diluting said mixed gas with nitrogen before feeding into a deoxygenation reactor. However, using nitrogen for dilution is high cost for reducing risk of combustion and explosion. Therefore, in order to improve the process safety of the hydro-catalytic deoxygenation technology of light hydrocarbons, it is necessary to develop the more efficient and safer methods for this system.

SUMMARY OF THE INVENTION

The present invention aims to overcome the problems of effectiveness and safety of the prior art, and provides a method for reducing the risk of burning and explosion in a deoxygenation process of an oxygen-containing gas.

The present inventors have surprisingly discovered in the researches that although gaseous alkane belongs to flammable and explosive gas, the introduction of gaseous alkane unexpectedly improves safety of the hydrocatalytic deoxygenation. Accordingly, in order to achieve the above object, the invention provides a method for reducing the risk of burning and explosion in a deoxygenation process of an oxygen-containing gas comprising unsaturated hydrocarbon and more than 0.5 vol. % oxygen, the method comprises: mixing hydrogen with the oxygen-containing gas from which the unsaturated hydrocarbon has been removed in the presence of a gaseous alkane, so that the oxygen contained in the mixed gas above undergoes a reaction with the hydrogen.

The invention also provides the use of a gaseous alkane for reducing the risk of burning and explosion during the deoxygenation of an oxygen-containing gas by means of the reaction of hydrogen with oxygen.

The present invention provides a method for reducing the risk of burning and explosion in a deoxygenation process of an oxygen-containing gas, the introduction of a gaseous alkane can reduce the risk of burning and explosion of mixed gas, reduce or eliminate nitrogen consumption, and is more efficient than nitrogen, the introduced gaseous alkane is also recyclable. The hydrocatalytic reaction is employed to promote the reaction of oxygen in the mixed gas with hydrogen to produce water, in order to fulfill the purpose of deoxygenating the oxygen-containing gas; in addition, the reaction product is clean, the other combustible gases in the oxygen-containing gas can be efficiently recovered, and the hydrocatalytic reaction can effectively inhibit the occurrence of carbon deposition on the catalyst surface and the generation of carbon oxide, and provide a strong endurance for fluctuation of the oxygen content in a raw gas. The technical solution of the invention is particularly suitable for the working condition such as the ultra-high oxygen concentration of tail gas, overtemperature of the reactor, and the other accidents that may occur during the process of facility operation.

DESCRIPTION OF REFERENCE SIGNS

Figure 1:
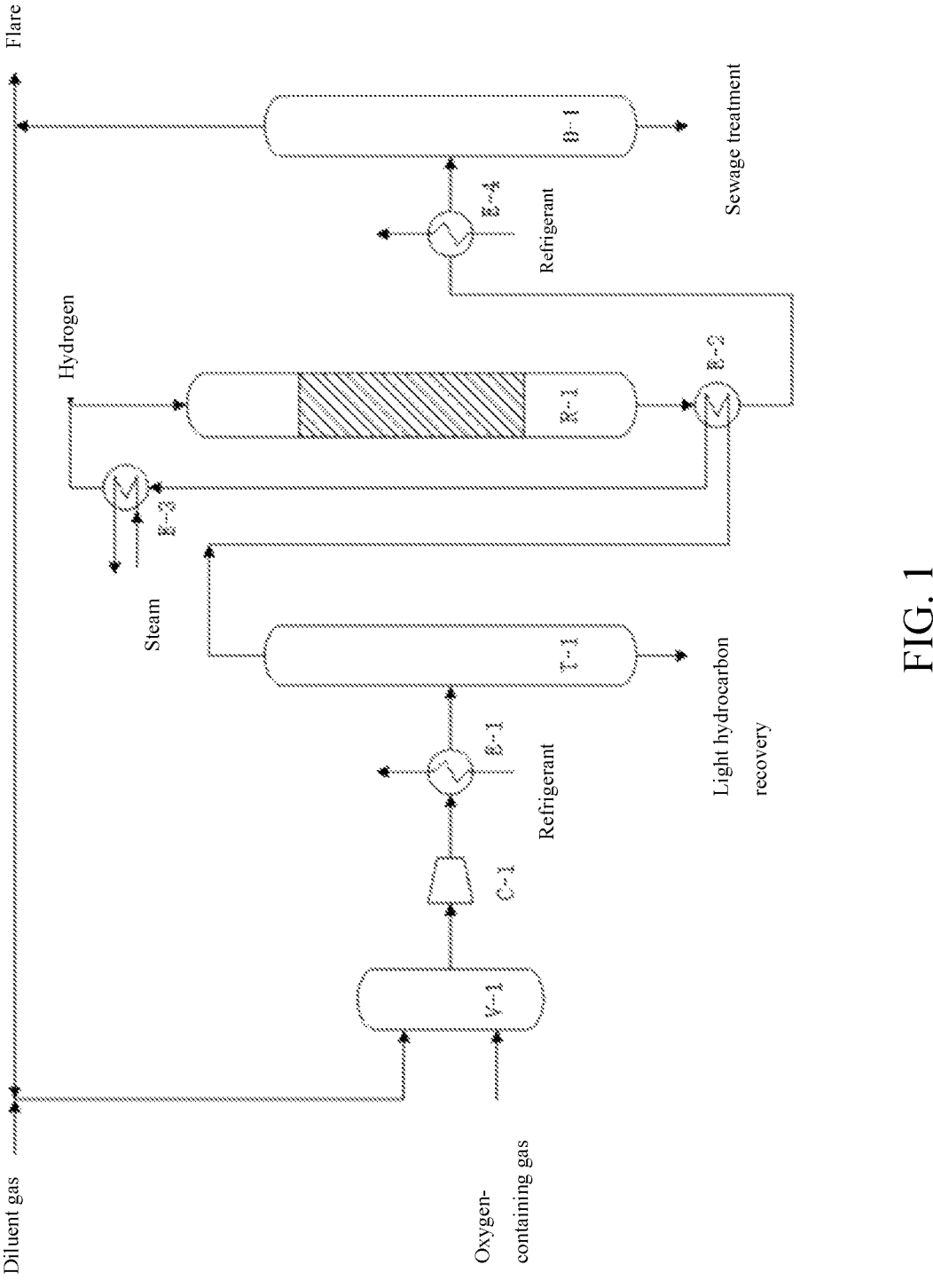
FIG. 1 illustrates a schematic view showing the structure of a system for carrying out a deoxygenation method of the invention in a preferred embodiment of the invention.

V-1: Buffer tank for pre-separation
C-1: Compressor
E-1, E-2, E-3, E-4: Heat exchanger
T-1: Separation tower
D-1: Separation tank
R-1: Deoxygenation reactor
1: First-stage feed inlet
2: Second-stage feed inlet
3: Third-stage feed inlet
4: Fourth-stage feed inlet
5: Safety valve
6: First-stage reaction bed
7: Second-stage reaction bed
8: Third-stage reaction bed
9: Fourth-stage reaction bed
10: Fifth-stage reaction bed
11: Discharge port
12: Packing layer
13: On-line detection system for oxygen content
14: Gas distributor
15: Manhole
16: Heat exchanger inlet
17: Heat exchanger outlet
18: Base
19: Pressure detection alarm
20: Flow control system

DESCRIPTION OF THE PREFERRED EMBODIMENT

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

Unless otherwise specified in the present invention, the term "removing a substance" in use does not mean eliminating the substance absolutely, but reducing the content of said substance to a lower level generally known by those skilled in the art. The term "pressure" refers to an absolute pressure.

The present invention provides a method for reducing the risk of burning and explosion in a deoxygenation process of an oxygen-containing gas comprising unsaturated hydrocarbon and more than 0.5 vol. % oxygen, wherein the method comprises: mixing hydrogen with the oxygen-containing gas from which the unsaturated hydrocarbon has been removed in the presence of a gaseous alkane, so that the oxygen contained in oxygen-containing gas undergoes an oxidation reaction with the hydrogen.

According to the present invention, the gaseous alkane may be introduced from outside. However, when the oxygen-containing gas contains gaseous alkane, it is maybe unnecessary to introduce gaseous alkane from outside, or the amount of gaseous alkane introduced from outside can be decreased accordingly. That is, the "gaseous alkane" in the present invention may refer to the gaseous alkane contained in an oxygen-containing gas only, or may refer to the gaseous alkane introduced from outside only, or a mixed gas of the gaseous alkane contained in an oxygen-containing gas and the gaseous alkane introduced from outside. In the present invention, the stabilizing gas or diluent gas merely refers to the gaseous alkane, thus the content of other non-active gases in the system of oxidation reaction (i.e., gases that do not react with any one of the hydrogen, oxygen and other combustible gases in the system, such as helium, nitrogen, argon, carbon dioxide, steam) is maintained at a low level, e.g., less than 10 vol. %, less than 5 vol. %, less than 3 vol. %, less than 2 vol. %, less than 1 vol. %, less than 0.5 vol. %, less than 0.05 vol. % or lower.

The invention does not impose particular requirement on the used amount of gaseous alkane, according to a preferred embodiment of the invention, the volume ratio of gaseous alkane to oxygen (contained in oxygen-containing gas) is not lower than 4, more preferably greater than 5, such as 6, 10, 12, 15, 18, 20, 22, 25, 30 or any ratio therebetween.

According to another preferred embodiment of the invention, the gaseous alkane makes up no less than 60 vol. %, such as 60 vol. %, 70 vol. %, 80 vol. %, 90 vol. %, 93 vol. %, 96 vol. %, 97 vol. %, 99 vol. % or any content therebetween of the total volume of gases in the system of oxidation reaction.

According to the invention, the term "gaseous alkane" refers to an alkane which is in a gaseous state under the operating condition of the present invention, it is preferable that the gaseous alkane is selected from the group consisting of C1-C4 (C1, C2, C3, C4) alkanes, including straight or branched chain alkanes, preferably at least one of methane, ethane and propane.

According to the invention, the oxygen-containing gas may also be an unsaturated hydrocarbon-containing gas, in order to avoid the adverse effects of unsaturated hydrocarbon on the oxidation reactions as much as possible, the method comprises removing unsaturated hydrocarbon from an oxygen-containing gas in the presence of a gaseous alkane, to obtain an oxygen-containing gas from which the unsaturated hydrocarbon has been removed. The unsaturated hydrocarbon may be removed by using the conventional methods in the prior art, such as at least one of direct gas-liquid separation, pressurization, absorption, and cooling rectification separation. Direct gas-liquid separation means that the oxygen-containing gas is fed directly into a vessel in which a separation of gas phase and liquid phase naturally occurs, without the application of pressure or temperature control during the process. The gas after removing unsaturated hydrocarbons mainly contains gaseous alkane and oxygen, and may comprise nitrogen, carbon monoxide, hydrogen and the like.

According to the invention, the oxygen content of the oxygen-containing gas may be greater than 0.5 vol. %, preferably greater than 2 vol. %, more preferably within a range of 3-99.5 vol. % (e.g., 0.6 vol. %, 1 vol. %, 2 vol. %,

5

2.5 vol. %, 2.8 vol. %, 3 vol. %, 4 vol. %, 5 vol. %, 6 vol. %, 10 vol. %, 20 vol. %, 30 vol. %, 40 vol. %, 50 vol. %, 55 vol. %, 60 vol. %, 70 vol. %, 80 vol. %, 90 vol. %, 93 vol. %, 96 vol. %, 99 vol. %, or any content therebetween). The content of other combustible gas (i.e., unsaturated hydrocarbon) in the oxygen-containing gas may be within a range of 0.5-99.99 vol. % (e.g., 0.1 vol. %, 1 vol. %, 10 vol. %, 20 vol. %, 30 vol. %, 40 vol. %, 50 vol. %, 60 vol. %, 70 vol. %, 80 vol. %, 90 vol. %, 93 vol. %, 96 vol. %, 99 vol. %, or any content therebetween).

The oxygen-containing gas in the present invention may further comprise an organic gas other than oxygen (e.g., methanol), and may also contain an inorganic gas, such as argon, helium, hydrogen, nitrogen, carbon monoxide. Therefore, the other combustible gas in the oxygen-containing gas is an combustible gas other than hydrogen and gaseous alkane, it may be selected from the group consisting of various common combustible organic gases and/or combustible inorganic gases other than gaseous alkane and hydrogen, including light hydrocarbons having no more than 4 carbon atoms, halogenated hydrocarbons having no more than 4 carbon atoms, alcohols having no more than 4 carbon atoms, ketones having no more than 4 carbon atoms, ethers having no more than 4 carbon atoms, carbon monoxide, etc.

According to a preferred embodiment of the invention, the other combustible gas is at least one selected from the group consisting of ethylene, ethylene oxide, propylene, propylene oxide, 1-butene, 2-butene, isobutylene, 1,3-butadiene, acetylene, propyne, 1-butyne, 2-butyne, vinyl chloride, 3-chloropropene, 1-chloropropane, 2-chloropropane and epoxy chloropropane.

According to the invention, the oxidation reaction refers to a reaction in which hydrogen and oxygen react to produce water. In this reaction, the used amount of hydrogen is not particularly required as long as it is possible to react oxygen in the oxygen-containing gas with hydrogen to produce water as much as possible, the hydrogen is used in an amount such that the volume ratio of hydrogen to oxygen (contained in oxygen-containing gas) is preferably within a range of 0.5-5, more preferably 1-3.

According to the present invention, the mixing (oxidation reaction) is carried out in the presence of a catalyst, the catalyst in the invention is not specifically directed to a catalyst as long as it has a function of catalyzing the reaction of oxygen with hydrogen to form water in a suitable temperature range, thereby achieving the purpose of removing oxygen. The catalyst is at least one selected from the group consisting of a precious metal catalyst (e.g., a platinum-based catalyst and/or a palladium-based catalyst) and a non-precious metal catalyst (e.g., a molybdenum-based catalyst, a copper-based catalyst, a nickel-based catalyst, a manganese-based catalyst). The active ingredient of the catalyst may be one or more of Pt, Pd, Ru, Rh, Ir, Ag, Fe, Ni, Mn, Cu, Ce, alkali metals and alkaline earth metals. The supporting amount of the active ingredient, based on the metal elements, may be 0.01-95 g/100 g of the carrier. The carrier of the catalyst may be one or more of alumina, silica-alumina molecular sieve, pure silica molecular sieve, phosphorus-aluminum molecular sieve, kaolin, diatomaceous earth and montmorillonite. The shape of a catalyst may be any of spherical, toothed, lacy ring, cylindrical, cloverleaf or quatrefoil shape.

According to a preferred embodiment of the invention, in order to further enhance the deoxygenation effect, reduce the hydrogenation selectivity of the hydrocarbon and extend the useful life of the catalyst, said catalyst comprises a carrier, and an active ingredient and a coagent supported on the carrier, the active ingredient comprises a precious metal, the coagent comprises an alkali metal and/or an alkaline earth metal, the catalyst satisfies the following formulae I and II:

$$0.8 < D1/(D1 + D2 + D3) < 0.98 \qquad \text{formula I}$$

$$5.2D_1 + 2.5D_2 + 160D_3 < W_1/W_2 < 100 \qquad \text{formula II}$$

wherein $D_1$ denotes a percentage of pore volume of the pores with pore diameter less than 20 nm in the total pore volume;

$D_2$ denotes a percentage of pore volume of the pores with pore diameter of 20-50 nm in the total pore volume;

$D_3$ denotes a percentage of pore volume of the pores with pore diameter larger than 50 nm in the total pore volume;

$W_1$ denotes a weight content of the coagent calculated in terms of metal element in the catalyst;

$W_2$ denotes a weight content of the active ingredient calculated in terms of metal element in the catalyst.

According to a preferred embodiment of the invention, the catalyst further satisfies: 80%<the percentage of pore volume of the pores with pore diameter less than 20 nm in the total pore volume (i.e., D1/(D1+D2+D3))<98%.

According to a preferred embodiment of the present invention, the catalyst also satisfies: 10<the ratio of the weight content of the coagent calculated in terms of metal element in the catalyst to the weight content of the active ingredient calculated in terms of metal element in the catalyst ($W_1/W_2$)<100.

According to the present invention, in order to further increase the oxygen removal rate, it is preferred that $D_1$ is within a range of 82-96% (e.g., 82%, 84%, 86%, 88%, 89%, 91%, 93%, 96% or any percentage therebetween). Preferably, $D_2$ is within a range of 0-20% (e.g., 1%, 2%, 4%, 4.6%, 8%, 8.5%, 9%, 11%, 12%, 15%, 17%, 18%, 19%, 20% or any percentage therebetween). Preferably, $D_3$ is within a range of 0-5% (e.g., 0.1%, 0.15%, 0.25%, 0.4%, 0.8%, 0.9%, 1%, 1.2%, 2%, 3%, 4%, 5% or any percentage therebetween).

According to the present invention, in order to further increase the oxygen removal rate, it is preferred that $W_1/W_2$=6-100, more preferably $W_1/W_2$=10-75 (such as 10, 12, 15, 20, 25, 30, 32, 38, 40, 50, 60, 68, 70, 72, 75 or any value therebetween).

According to the present invention, the contents of carrier, active ingredient and coagent are not particularly defined. Preferably, the amount of active ingredient calculated in terms of metal element is 0.01-5 wt. %, more preferably 0.1-1 wt. %, based on the total amount of catalyst.

Preferably, the amount of the coagent calculated in terms of metal element is within a range of 0.1-20 wt. %, more preferably 5-10 wt. %, based on the total amount of catalyst.

Preferably, the carrier is contained in an amount of 75-99.8 wt. %, more preferably 85-94 wt. %, based on the total amount of catalyst.

Unless otherwise specified in the invention, the total amount of catalyst=a content of the active ingredient calculated in terms of metal element+a content of the coagent calculated in terms of metal element+a content of the carrier.

According to the present invention, it is preferable that a weight ratio of the coagent calculated in terms of metal element to the active ingredient calculated in terms of metal element is 6-100:1.

According to the present invention, it is preferable that the coagent is an alkali metal and alkaline earth metal, a weight ratio of the alkali metal to the alkaline earth metal is 5-10:1, a weight ratio of the alkali metal to the alkaline earth metal is more preferably 6-9:1. The deoxygenation performance of the catalyst can be further improved by combining the alkali metal with the alkaline earth metal. Further preferably, the coagent is at least one selected from the group consisting of Na, K, and Cs and at least one selected from the group consisting of Mg, Ca, and Ba; most preferably a combination of Na and Mg, or a combination of K and Ca.

According to the present invention, the active ingredient is selected from precious metals commonly used in the field, preferably, the active ingredient is at least one selected from the group consisting of Pt, Pd, Ru, Rh, Ag and Ir; more preferably, the active ingredient is at least one selected from the group consisting of Pt, Pd and Ru.

According to another preferred embodiment of the invention, the catalyst may further comprise a group VIII transition metal from the fourth period, more preferably Fe. The weight ratio of the group VIII transition metal from the fourth period to the active ingredients is within the range of 3-50:1. The introduction of a group VIII transition metal from the fourth period can further improve sulphur resistance of the catalyst. In the present invention, when the catalyst comprises a group VIII transition metal from the fourth period, $W_1$ merely represents the weight content of the alkali metal and the alkaline earth metal, excluding the weight content of the group VIII transition metal from the fourth period.

According to the invention, it is preferable that the carrier is at least one selected from the group consisting of alumina (gamma-alumina), silica, titania and carbon nanotube.

According to the invention, it is preferable that the catalyst has a specific surface area within a range of 120-260 $m^2/g$. Preferably, the catalyst has a pore volume within a range of 0.4-0.8 $cm^3/g$. Preferably, the catalyst has an average pore diameter within a range of 6-25 nm.

The invention further provides a method for preparing the catalyst, the method comprises the following steps: subjecting a carrier precursor and a modifier to a first calcination at the temperature of 450-1,000° C.; then supporting an active ingredient precursor and a coagent precursor onto the first calcination product to obtain a catalyst precursor; subsequently subjecting the catalyst precursor to a second calcination; wherein the modifier is ammonium chloride and/or urea.

Preferably, the carrier precursor is at least one selected from the group consisting of pseudoboehmite, silica sol, sodium silicate, alumina sol, tetrabutyl titanate and activated carbon.

Preferably, the first calcination is performed for 1-10 h.

Preferably, the first calcination is carried out in air.

Preferably, the method of first calcination is as follows: heating the carrier precursor and the modifier to a temperature of 450-1,000° C. (e.g., 450° C., 490° C., 510° C., 550° C., 590° C., 610° C., 640° C., 660° C., 700° C., 800° C., 900° C., 1,000° C., or any temperature therebetween) at a heating rate of 200-600° C./h (e.g., 200° C./h, 210° C./h, 250° C./h, 290° C./h, 310° C./h, 350° C./h, 390° C./h, 410° C./h, 500° C./h, 600° C./h, or any heating rate therebetween), and holding at this temperature for 1-10 h (e.g., 1 h, 2 h, 3 h, 4 h, 5 h, 6 h, 8 h, 10 h, or any time therebetween).

Preferably, a weight ratio of the carrier precursor to the modifier is 5-10:1.

In aforementioned preparation method of the invention, in order to obtain the aforesaid catalyst comprising an active ingredient and a coagent, those skilled in the art can select the active ingredient precursor and the coagent precursor according to the kind of the active ingredient and the coagent, these information will not be further described herein.

Preferably, the active ingredient precursor is at least one selected from the group consisting of nitrate, chloride, acetate and metal acetylacetonate of the active ingredient.

More preferably, the active ingredient precursor is selected from palladium chloride and/or chloroplatinic acid.

Preferably, the coagent precursor is at least one selected from the group consisting of a nitrate, chloride and acetate of the coagent.

Preferably, the active ingredient precursor and the coagent precursor are used in such amounts that the produced catalyst contain an active ingredient calculated in terms of metal element in an amount of 0.01-5 wt. %, a coagent calculated in terms of metal element in an amount of 0.1-20 wt. %, and a carrier in an amount of 75-99.8 wt. %; more preferably, the produced catalyst contain an active ingredient calculated in terms of metal element in an amount of 0.1-1 wt. %, a coagent calculated in terms of metal element in an amount of 5-10 wt. %, and a carrier in an amount of 85-94 wt. %

Preferably, the active ingredient precursor and the coagent precursor are used in such amounts that the produced catalyst has a weight ratio of the active ingredient calculated in terms of metal element to the coagent calculated in terms of metal element within a range of 6-100, preferably 10-75.

Preferably, the used amounts of an alkali metal precursor and an alkaline earth metal precursor in the coagent precursor cause that in the produced catalyst, a weight ratio of the alkali metal to the alkaline earth metal is 5-10:1; more preferably, a weight ratio of the alkali metal to the alkaline earth metal is 6-9:1.

Preferably, the temperature of second calcination is 0-50° C. lower than the temperature of first calcination. Preferably, the heating rate of the second calcination is 140-240° C./h lower than the heating rate of the first calcination. More preferably, the method of second calcination comprises: performing the second calcination at 300-800° C. for 1-5 h; or initially heating to 300-800° C. at a heating rate of 60-160° C./h, then holding at this temperature for 1-5 h.

Preferably, the second calcination is carried out in air.

Preferably, the method of supporting the active ingredient precursor and the coagent precursor onto the carrier is an impregnation method; more preferably, the method comprises the process of supporting the active ingredient precursor and the coagent precursor onto the carrier:

(1) formulating an impregnating solution containing an active ingredient precursor and a coagent precursor, said impregnating solution has a pH within a range of 0.5-4 or 9-13;

(2) impregnating the carrier in the impregnating solution, and subjecting the impregnated carrier to an optional drying step.

More preferably, the process of formulating an impregnating solution containing an active ingredient precursor and a coagent precursor comprises: dissolving the active ingredient precursor in an acid solution or an alkaline solution, then mixing with the coagent precursor, subsequently adding water to adjust the system pH to a range of 0.5-4 or 9-13. Preferably, the acid solution is at least one selected from the group consisting of hydrochloric acid, nitric acid and acetic acid, and/or the alkaline solution is at least one selected from the group consisting of ammonium hydroxide, sodium hydroxide and sodium carbonate.

More preferably, the impregnating time is 0.5-10 h.

According to another preferred embodiment of the present invention, the preparation method of the catalyst may further comprise a step of supporting the group VIII transition metal from the fourth period. The method of supporting the group VIII transition metal from the fourth period may be conventional impregnation method, but preferably, contacting the group VIII transition metal from the fourth period and the modifier with the carrier precursor and performing the first calcination, that is, preferably impregnating the carrier precursor in an impregnating solution containing the modifier and the precursor for group VIII transition metal from the fourth period, then drying the impregnated carrier precursor and performing the first calcination at a temperature of 450-1,000° C. The group VIII transition metal from the fourth period is preferably Fe. Preferably, the group VIII transition metal precursor from the fourth period is used in an amount such that in the prepared catalyst, a weight ratio of the transition metal from the fourth period to the active ingredient is within a range of 3-50:1.

According to the present invention, there is no particular requirements on the condition of mixing (oxidation reaction) so long as the oxidation reaction can occur, and preferably, the condition of mixing (oxidation reaction) cause that the oxygen content of the gases after the reaction is 1.5 vol. % or less, and more preferably 0.5 vol. % or less. According to a more preferred embodiment of the invention, the temperature of oxidation reaction is below the light-off temperature for the catalytic combustion of gaseous alkane, so as to avoid the catalytic combustion reaction of the gaseous alkane with oxygen. According to a more preferred embodiment of the present invention, the condition of oxidation reaction comprise: the gas hourly space velocity in terms of total volume is within a range of 2,000-20,000 h$^{-1}$, the pressure within a range of 0.1-10 MPa, and the temperature within a range of 30-600° C.

According to a preferred embodiment of the present invention, the gaseous alkane is methane, and the condition of oxidation reaction comprise: the gas hourly space velocity in terms of total volume is within a range of 2,000-20,000 h$^{-1}$, the pressure within a range of 0.1-5 MPa, and the temperature within a range of 30-500° C. (more preferably 30-150° C.).

According to a preferred embodiment of the present invention, the gaseous alkane is ethane, and the condition of oxidation reaction comprise: the gas hourly space velocity in terms of total volume is within a range of 2,000-15,000 h$^{-1}$, the pressure within a range of 0.1-4.5 MPa, and the temperature within a range of 30-400° C. (more preferably 30-120° C.).

According to a preferred embodiment of the present invention, the gaseous alkane is propane, and the condition of oxidation reaction comprise: the gas hourly space velocity in terms of total volume is within a range of 2,000-10,000 h$^{-1}$, the pressure within a range of 0.1-4 MPa, and the temperature within a range of 30-350° C. (more preferably 30-100° C.).

According to the invention, in order to further improve the efficiency of oxidation reaction, the method may further comprise the following steps: prior to contacting the oxygen-containing gas with hydrogen, mixing the oxygen-containing gas with hydrogen, and preheating the mixed gases, subjecting the preheated mixed gases to a reaction under the condition of performing oxidation reaction with hydrogen, wherein the preheating raises the temperature of the gases to reach an activation temperature (typically 50-300° C.) of the catalyst in use.

According to the invention, the residual gas after the reaction is mainly gaseous alkane, the direct reuse of said residual gas will further reduce the energy consumption of the treatment. Therefore, according to a preferred embodiment of the invention, the method further comprises: recycling the gas which does not participate the oxidation reaction (i.e., residual gas after the oxidation reaction) as gaseous alkane. The gas which does not participate the oxidation reaction is condensed and the temperature may be reduced to 45° C. or lower and reused by circulation pumping to the step of unsaturated hydrocarbon removal (e.g. gas-liquid separation).

In accordance with the present invention, the water generated in the oxidation reaction can be periodically discharged to a waste water collection system (sewage treatment system).

In the present invention, the oxidation reaction may be carried out in a fixed bed reactor, which may be, for example, an adiabatic bed, a drum tube reactor, etc.

In accordance with a preferred embodiment of the invention, the method includes a multi-stage oxidation reaction, that is, the oxygen-containing gas (an oxygen-containing gas from which the unsaturated hydrocarbon has been removed) may be divided into a plurality of parts, and the oxidation reaction is carried out in a stepwise manner, which further improves the deoxygenation efficiency, reduces the circulation dosage of gaseous alkane, and facilitates better control of the temperature of said oxidation reaction, prevents temperature runaway of the reactor, reduces the phenomenon of carbon deposition on the catalyst, improves the service life of the catalyst, and extends the run time of system.

In a preferred embodiment of the invention comprising a multi-stage oxidation reaction, the method comprises: dividing a mixed gas comprising hydrogen and oxygen into n parts, and subjecting the 1-n parts of the mixed gas to oxidation reaction according to the following steps:

(a) subjecting the first part of mixed gas to an oxidation reaction in the presence of a gaseous alkane and a first catalyst, to obtain a first part of deoxygenated gas;

(b) subjecting the second part of mixed gas and the first part of deoxygenated gas obtained in step (a) to an oxidation reaction in the presence of a gaseous alkane and a second catalyst, to obtain a second part of deoxygenated gas; and operating according to said pattern until the n'th part of deoxygenated gas is obtained.

In a preferred embodiment of the invention comprising a multi-stage oxidation reaction, the used amounts or proportions of hydrogen and oxygen in each part of mixed gas may be as previously mentioned, or be suitably adjusted according to the condition of individual stage of the system of oxidation reaction such that the used amounts or proportions of hydrogen and oxygen in the system of oxidation reaction meet the aforementioned requirements, so does the gaseous alkane. It shall be particularly indicated that the mixed gas may refer to the mixed gas having a pre-mixed components, or may refer to that reaction systems that are mixed in real time during the oxidation reaction. Similarly, the gaseous alkane may be introduced from the outside, or may be carried by the oxygen-containing gas per se, in the multi-stage oxidation reaction, the gaseous alkane of the latter step may be introduced, at least in part, by the preceding step. Each part of the mixed gas may also contain gaseous alkane, but the content of gaseous alkane may vary, but it is preferable that the content of gaseous alkane causes that the gaseous alkane makes up no less than 60 vol. % (e.g., 60 vol. %, 70 vol. %, 80 vol. %, 90 vol. %, 93 vol. %, 96 vol. %, 97 vol. %, 99 vol. % or any content therebetween) of the total volume of gases in the system of oxidation reaction in each stage, thereby providing improved protection against the burning and explosion.

In a preferred embodiment of the invention comprising a multi-stage oxidation reaction, in order to better avoid the burning and explosion, the oxygen-containing gas (an oxygen-containing gas from which the unsaturated hydrocarbon has been removed) is blending with the gaseous alkane before it is mixed with hydrogen.

In a preferred embodiment of the invention comprising a multi-stage oxidation reaction, n may be 2 or any integer greater than 2, preferably n is an integer of 3-20.

In a preferred embodiment of the invention comprising a multi-stage oxidation reaction, the oxygen content c in the system of oxidation reaction in each step satisfy that $c \geq 15$ vol. %, and $20 \geq n > 12$; or the oxygen content c in the system of oxidation reaction in each step satisfy that 15 vol. %$> c \geq 10$ vol. %, and $12 \geq n > 8$; or the oxygen content c in the system of oxidation reaction in each step satisfy that 10 vol. %$> c \geq 6$ vol. %, and $8 \geq n > 5$; or the oxygen content c in the system of oxidation reaction in each step satisfy that $c < 6$ vol. %, and $5 \geq n \geq 1$. Such a way of determining n based on the oxygen content of the system of oxidation reaction in each step is particularly advantageous in preventing temperature runaway, increasing the throughput of gases, reducing the carbon deposition amount of the catalyst, and extending the service life of the catalyst under the circumstance of low dosage of gaseous alkane.

In a preferred embodiment of the invention comprising a multi-stage oxidation reaction, the oxygen content in the mixed gas is greater than 5 vol. %, n=4, the volume of a first part of the mixed gas makes up 10-40% of the total volume of the mixed gas in each part, the volume of a second part of the mixed gas makes up 30-60% of the total volume of the mixed gas in each part, the volume of a third part of the mixed gas makes up 20-40% of the total volume of the mixed gas in each part, and the volume of a fourth part of the mixed gas makes up 1-10% of the total volume of the mixed gas in each part.

In another preferred embodiment of the invention comprising a multi-stage oxidation reaction, the oxygen content in the mixed gas is 2-5 vol. %, n=4, the volume of a first part of the mixed gas makes up 30-60% of the total volume of the mixed gas in each part, the volume of a second part of the mixed gas makes up 20-50% of the total volume of the mixed gas in each part, the volume of a third part of the mixed gas makes up 20-30% of the total volume of the mixed gas in each part, and the volume of a fourth part of the mixed gas makes up 1-20% of the total volume of the mixed gas in each part.

In another preferred embodiment of the invention comprising a multi-stage oxidation reaction, the oxygen content in the mixed gas is less than 2 vol. %, n=4, the volume of a first part of the mixed gas makes up 40-65% of the total volume of the mixed gas in each part, the volume of a second part of the mixed gas makes up 25-40% of the total volume of the mixed gas in each part, the volume of a third part of the mixed gas makes up 10-30% of the total volume of the mixed gas in each part, and the volume of a fourth part of the mixed gas makes up 1-25% of the total volume of the mixed gas in each part.

In an embodiment of the invention comprising a multi-stage oxidation reaction, the temperature of oxidation reaction in each step may be controlled within the range of 30-380° C.

In an embodiment of the invention comprising a multi-stage oxidation reaction, the pressure of oxidation reaction in each step may be controlled within the range of 0.3-5 MPa.

In an embodiment of the invention comprising a multi-stage oxidation reaction, the gas hourly space velocity in terms of total volume of oxidation reaction in each step may be controlled within the range of 500-45,000 $h^{-1}$.

In an embodiment of the invention comprising a multi-stage oxidation reaction, the condition of oxidation reaction in each step may be the same or different.

In an embodiment of the invention comprising a multi-stage oxidation reaction, in order to ensure that the oxygen content of the gas after oxidation reaction is maintained at a relatively low level, the method may further comprise: subjecting the n'th part of deoxygenated gas to an oxidation reaction in the presence of a post-treatment catalyst.

In an embodiment of the invention comprising a multi-stage oxidation reaction, the catalysts in each of the aforesaid steps (including the first catalyst, the second catalyst, the third catalyst . . . , the post-treatment catalyst) may be the catalysts commonly used in the art for catalyzing the reaction of oxygen with hydrogen to generate water, and can also be the catalysts recited in aforementioned preferred embodiments, the catalysts in each step may be the same or different.

Figure 2:
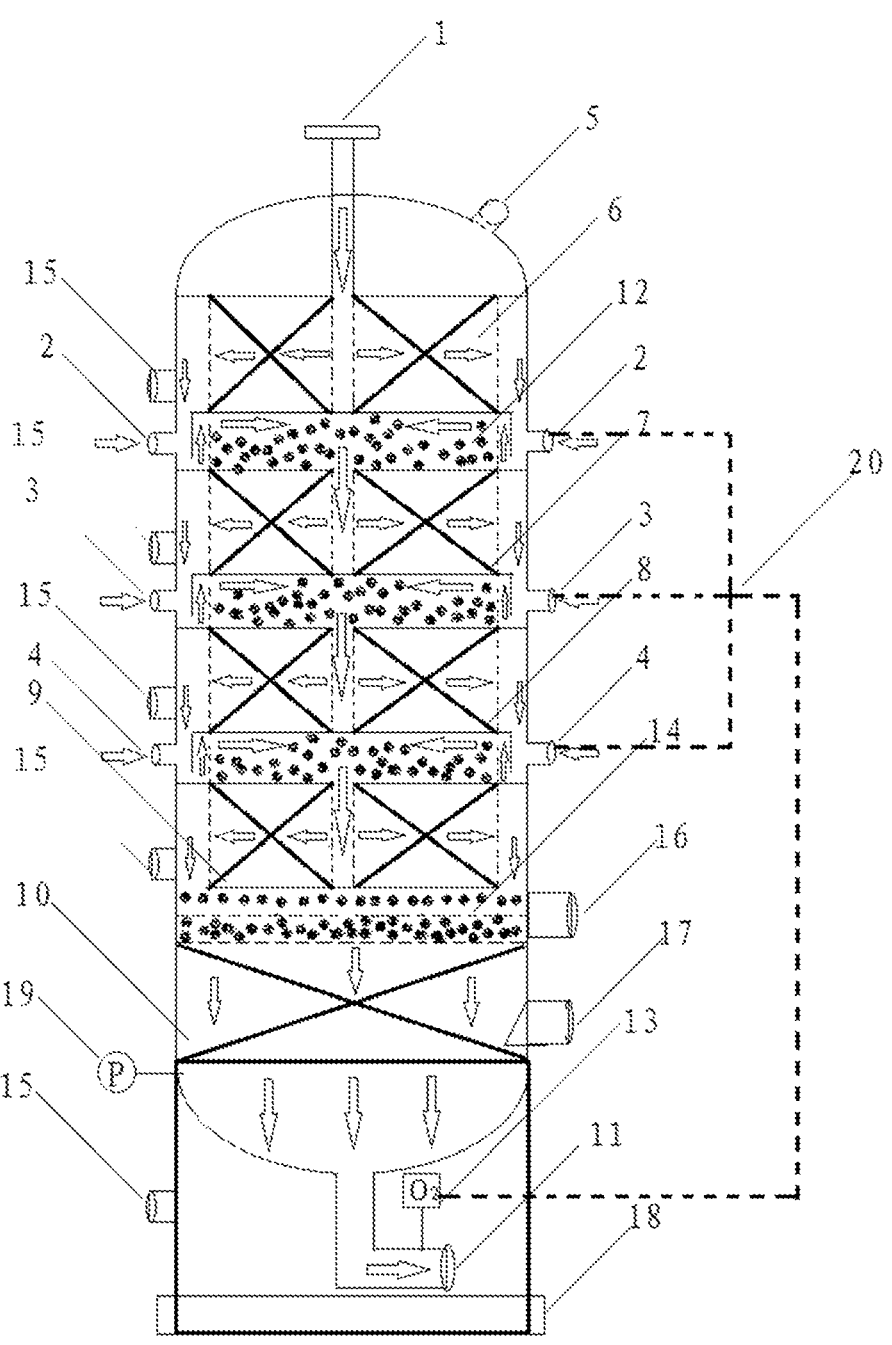
FIG. 2 illustrates a schematic view showing the structure of a system for carrying out a deoxygenation method of the invention in another preferred embodiment of the invention.

The multi-stage oxidation reaction of the present invention can be performed in a multi-stage reactor (as shown in FIG. 2) comprising a structure as follows: the main reactor is provided with a first-stage feed inlet 1, a second-stage feed inlet 2, a third-stage feed inlet 3, a fourth-stage feed inlet 4 and a discharge port 11 sequentially from top to bottom; an inside of the main reactor is arranged with a first-stage reaction bed 6, a second-stage reaction bed 7, a third-stage reaction bed 8, a fourth-stage reaction bed 9, and a fifth-stage reaction bed 10 sequentially from top to bottom; and the corresponding clapboards are arranged in the main reactor so that the raw gas introduced from the first-stage feed inlet 1 can flow through the first-stage reaction bed 6 and then flow through the second-stage reaction bed 7 together with the raw gas introduced from the second-stage feed inlet 2; the gas flowing through the second-stage reaction bed 7 then flows through the third-stage reaction bed 8 together with the raw gas introduced from the third-stage feed inlet 3; the gas flowing through the third-stage reaction bed 8 then flows through the fourth-stage reaction bed 9 together with the raw gas introduced from the fourth-stage feed inlet 4; the gas flowing through the fourth-stage reaction bed 9 further flows through the fifth-stage reaction bed 10 and discharged through the discharge port 11. A packing layer 12 is further arranged between each reaction bed in the main reactor, such that the gas from the upstream stage reaction bed passes through the corresponding packing layer and then flows through the next-stage reaction bed, and the packing layer can make the gas more evenly distributed, thereby further improving the deoxygenation efficiency and increasing the deoxygenation effect. A safety valve 5 may be arranged at the top of the main reactor for the purpose of timely discharging the gas in the main reactor. A corresponding manhole 15 can be arranged on the main reactor for the sake of cleaning and maintaining each stage of the reaction bed. The main reactor can further comprise a base 18. A pressure detection alarm 19 may be further arranged in the main reactor, wherein the pressure detection alarm can be used for detecting a pressure in the main reactor, and emits an alarm when a pressure in the main reactor exceeds a predetermined threshold. In order to ensure that the gas distribution is more uniform and further improve the deoxygenation efficiency and increasing the deoxygenation effect, the main reactor can further comprise a gas distributor 14 arranged upstream the fifth-stage reaction bed 10. A heat exchanger which can carry out a heat exchange with the fifth-stage reaction bed 10 may be arranged in the fifth-stage reaction bed 10, so that the fifth-stage reaction bed is effectively cooled, such that the catalyst on the fifth-stage reaction bed is not prone to suffer from the carbon deposition, and the service life of the catalyst is extended. The heat exchanger is provided with a heat exchanger inlet 16 for introducing a cooling medium and a heat exchanger outlet 17 for discharging the cooling medium after the heat exchange. An on-line detection system for oxygen content 13 and a flow control system 20 can be further arranged in the main reactor, in order to facilitate detection of the oxygen content and control of the feedstock flow rate.

The invention also provides the use of a gaseous alkane for reducing the risk of burning and explosion in the deoxygenation of an oxygen-containing gas by the reaction of hydrogen with oxygen. The specific species or composi- (2) The feeding was conducted according to stoichiometric ratio of components in a catalyst, palladium chloride was dissolved in dilute hydrochloric acid having a concentration of 0.1 mol/L, after complete dissolution, sodium nitrate and magnesium nitrate were added, stirred uniformly, water was then introduced to adjust pH to 3 to obtain an impregnating solution.

(3) Preparation of a catalyst C1: the first calcination product was placed in an impregnating solution and impregnated for 5 h, after the impregnation was complete, it was stirred and steamed at 120° C., and then dried in an oven at 80° C. for 12 h to obtain a catalyst precursor; then it was calcinated in air under the calcination condition comprising: the temperature was raised to 500° C. at a heating rate of 100° C./h, then maintained at this temperature for 3 h.

Preparation Examples 2-3

The preparation of catalysts C2 and C3 was carried out according to the method of Preparation Example 1, except that the stoichiometric ratios of the components in the catalysts were different from that of Preparation Example 1, and the preparation condition of the catalysts was different, as specifically shown in Table 1.

TABLE 1

| Step | Items | Preparation Example 2 | Preparation Example 3 |
|---|---|---|---|
| (1) | Modifier | Urea | Ammonium chloride |
| | Carrier precursor | Pseudoboehmite | Pseudoboehmite |
| | Weight ratio of carrier precursor and modifier | 8:1 | 10:1 |
| | Heating rate of calcination | 200° C./h | 400° C./h |
| | Calcination temperature | 650° C. | 600° C. |
| | Calcination time | 5 h | 2 h |
| (2) | Active ingredient precursor | Chloroplatinic acid | Palladium chloride |
| | Acid solution | Dilute hydrochloric acid with a concentration of 0.1 mol/L | Dilute hydrochloric acid with a concentration of 0.1 mol/L |
| | Alkaline metal precursor | Sodium nitrate | Sodium nitrate |
| | Alkaline earth metal precursor | Magnesium nitrate | Calcium nitrate |
| | pH of the impregnating solution | 1 | 3 |
| (3) | Impregnation time | 5 h | 5 h |
| | Heating rate of calcination | 60° C./h | 160° C./h |
| | Calcination temperature | 600° C. | 600° C. |
| | Calcination time | 5 h | 3 h | tions of the gaseous alkane and oxygen-containing gas are as described above and will not be described in detail herein.

The invention will be described in detail below with reference to Examples. In the following examples, the analysis method of the gas composition is gas chromatographic method; the calculation formula for the conversion rate of oxygen is as follows: conversion rate of oxygen=(the volume of oxygen contained in oxygen-containing gas−the volume of oxygen contained in the reaction product)/the volume of oxygen contained in oxygen-containing gas× 100%.

Preparation Example 1

(1) The pseudobochmite powder and the ammonium chloride in solid form were mixed according to a weight ratio of 5:1, the mixture was heated at a heating rate of 300° C./h to 500° C., and calcinated at this temperature for 5 h to obtain a first calcination product.

Preparation Example 4

Preparation of catalyst C4 was carried out according to the method of Preparation Example 1, except that the stoichiometric ratio of the components in the catalyst was different from that of Preparation Example 1, and the procedure of step (1) was different: $Fe(NO_3)_3$ and urea were dissolved in deionized water to formulate an impregnating solution, pseudoboehmite powder was then placed in the impregnating solution and impregnated for 3 h, it was stirred and steamed at 80° C., and then calcinated at 500° C. for 7 h to obtain a first calcination product.

Preparation Example 5

Preparation of catalyst C5 was carried out according to the method of Preparation Example 1, except that the feeding amount of the coagent caused that a weight ratio of sodium nitrate calculated in terms of metal element to magnesium nitrate calculated in terms of metal element was 1:1.

Preparation Example 6

Preparation of catalyst C6 was carried out according to the method of Preparing Example 1, except that magnesium nitrate was replaced with sodium nitrate.

Preparation Example 7

Preparation of catalyst C7 was carried out according to the method of Preparing Example 1, except that sodium nitrate was replaced with magnesium nitrate.

Preparation Example 8

Preparation of catalyst C8 was carried out according to the method of Preparation Example 1, except that the feeding amount of the coagent caused that a weight ratio of sodium nitrate calculated in terms of metal element to magnesium nitrate calculated in terms of metal element was 1:5.

Comparative Preparation Example 1

The preparation of catalyst C9 was carried out according to the method of Preparation Example 1, except that the pseudoboehmite was calcinated directly at 1,200° C. for 5 h to obtain a carrier, replacing the first calcination product for impregnate.

Comparative Preparation Example 2

The preparation of catalyst C10 was carried out according to the method of Preparation Example 1, except that the ammonium chloride in solid form was replaced with N,N-dimethylformamide.

Comparative Preparation Example 3

The preparation of catalyst C11 was carried out according to the method of Preparation Example 1, except that magnesium nitrate and sodium nitrate were replaced with ferric nitrate.

Test Example 1

The catalysts prepared in aforementioned Preparation Examples and Comparative Preparation Examples were characterized with the structural parameters, the results were shown in Table 2. The elemental composition of the catalysts prepared in aforementioned Preparation Examples and Comparative Preparation Examples were characterized, the content of metal elements in the active ingredient and the content of metal elements in the coagent were shown in Table 2, and the balance was the carrier.

Tests of the specific surface area and pore size distribution: the analysis of specific surface area and pore structure was performed using a physical adsorbent instrument TriStar® II 3020 manufactured by Micromeritics, USA. The specific test condition included that the surface area and pore structure were measured using the $N_2$ adsorption method at the temperature of −196° C. (liquid nitrogen temperature), the samples were vacuumized and pretreated at 300° C. to a pressure less than $10^{-3}$ Pa, and the test method was a static method. The specific surface area and pore structure were calculated using the BET method based on adsorption isotherms.

The content of ingredients in the catalyst was tested using the ICP-AES method.

TABLE 2

| | Specific surface area (m²/g) | Pore volume (cm³/g) | $D_1$ (%) | $D_2$ (%) | $D_3$ (%) | Average pore diameter (nm) | $W_1$ (wt. %) | $W_2$ (wt. %) | R | Whether satisfies formula I | Whether satisfies formula II |
|---|---|---|---|---|---|---|---|---|---|---|---|
| Preparation Example 1 | 158 | 0.64 | 85 | 14 | 1 | 12 | 7 | 0.2 | 7 | Yes | Yes |
| Preparation Example 2 | 176 | 0.52 | 95 | 4.9 | 0.1 | 12 | 7 | 0.1 | 6 | Yes | Yes |
| Preparation Example 3 | 240 | 0.68 | 90 | 10 | 0 | 9 | 10 | 1.0 | 9 | Yes | Yes |
| Preparation Example 4 | 165 | 0.46 | 92 | 7.8 | 0.2 | 8 | 10 | 1.0 | 7 | Yes | Yes |
| Preparation Example 5 | 145 | 0.45 | 82 | 17.8 | 0.2 | 10 | 7 | 0.2 | / | Yes | Yes |
| Preparation Example 6 | 180 | 0.49 | 87 | 13 | 0 | 8 | 7 | 0.2 | / | Yes | Yes |
| Preparation Example 7 | 245 | 0.48 | 90 | 8.8 | 0.2 | 11 | 7 | 0.2 | / | Yes | Yes |
| Preparation Example 8 | 156 | 0.42 | 90 | 10 | 0 | 9 | 7 | 0.2 | / | Yes | Yes |
| Comparative Preparation Example 1 | 5 | 0.08 | 0 | 0 | 100 | 3 | 10 | 0.8 | / | No | No |
| Comparative Preparation Example 2 | 150 | 0.24 | 68 | 30 | 2 | 30 | 0.7 | 0.3 | / | No | No |
| Comparative Preparation Example 3 | 126 | 0.42 | 86 | 14 | 0 | 8 | 0 | 0.2 | / | Yes | No |

Note:
R denotes the weight ratio of alkali metal to alkaline earth metal.

It can be derived from the further analysis that the ratios of the content of Fe to $W_2$ in Preparation Example 4 and Comparative Preparation Example 3 were 3 and 50 respectively.

Test Example 2

(1) The catalysts prepared in aforementioned Preparation Examples and Comparative Preparation Examples were used for deoxygenation of an oxygen-containing gas, the condition of deoxygenation included: a reaction temperature of 60° C., a pressure of 0.3 MPa, a gas hourly space velocity in terms of volume of 5,000 h$^{-1}$, the oxygen-containing gas contained oxygen and hydrocarbon gas, the methane (gaseous alkane) were mixed with hydrogen (reducing gas) and the oxygen-containing gas, the mixed gas had a volume ratio of hydrogen to oxygen being 2.2:1, and a volume ratio of methane to oxygen being 15. The oxygen concentration in the mixed gas and the oxygen concentration after reaction were shown in Table 3.

(2) The catalysts prepared in aforementioned Preparation Examples and Comparative Preparation Examples were subjected to a service life test and measurement, the test was performed according to the condition of the deoxygenation in step (1), the service life of the catalysts was characterized by the time of catalyst deactivation, the catalyst deactivation was defined as follows: when the oxygen conversion rate of the catalyst was lower than 80% of the initial conversion rate, the catalyst was deemed to have been deactivated, in the meanwhile, the total time period of running the deoxygenation was the service life of the catalyst, the term "greater than a certain time period" referred to that the catalyst was not deactivated when the treatment time reached the time period, but the experiment was not continued any more. The results were shown in Table 3.

As shown from the results of Table 3, the deoxygenation performance of the catalysts prepared in the preferred embodiment of the invention was further enhanced, in addition, the selectivity and service life of the catalysts were further improved.

Examples 1-3 and Comparative Examples 1-2

The tail gas (oxygen-containing gas) was treated in accordance with the steps shown in FIG. 1, the specific operations were as follows:

The oxygen-containing gas was mixed with gaseous alkane in a buffer tank for pre-separation V-1 such that the content of gaseous alkane in the pre-mixed gas was not less than 90%. The pre-mixed gas was pressurized by a first compressor C-1, and cooled by a first heat exchanger E-1, then introduced into a separation tower T-1, the separation of unsaturated hydrocarbons with C2 or more and the noncondensable gas (gaseous alkane, oxygen) was performed in the separation tower T-1, the condensed hydrocarbons were discharged from the bottom of the separation tower T-1 and delivered to the light hydrocarbon recovery system; the noncondensable gas composed of gaseous alkane and oxygen was ejected from the top of the separation tower T-1 and exchanged heat with the deoxygenation product in a second heat exchanger E-2, then heated by steam in a third heat exchanger E-3 to the activation temperature for the deoxygenation reaction; the gas was mixed with hydrogen at an inlet of the deoxygenation reactor R-1 (hydrogen was used in an amount such that the volume ratio of hydrogen to oxygen was 2.2) and then entered the reactor, contacted with a catalyst in the deoxygenation reactor R-1 to carry out the hydrocatalytic deoxygenation reaction, the reaction product was removed from the catalyst bed and exited from the bottom of the deoxygenation reactor R-1. The product initially exchanged heat in the second heat exchanger E-2

TABLE 3

| | $O_2$ concentration in oxygen-containing gas (vol. %) | Hydrocarbon gas | Hydrogenation selectivity of hydrocarbon (%) | $O_2$ concentration after treatment (vol. %) | Service life (h) |
|---|---|---|---|---|---|
| Preparation Example 1 | 3 | Propylene | <10% | <0.2 | >1,000 |
| Preparation Example 2 | 5 | Propylene | <10% | <0.5 | >800 |
| Preparation Example 3 | 3 | Propylene | <10% | <0.1 | >800 |
| Preparation Example 4 | 3 | Propylene | <10% | <0.1 | >800 |
| Preparation Example 5 | 3 | Propylene | <15% | <1 | <500 |
| Preparation Example 6 | 3 | Propylene | <15% | <1 | <500 |
| Preparation Example 7 | 3 | Propylene | <15% | <1 | <500 |
| Preparation Example 8 | 3 | Propylene | <15% | <1 | <500 |
| Comparative Preparation Example 1 | 3 | Propylene | About 30% | <2 | <400 |
| Comparative Preparation Example 2 | 3 | Propylene | About 20% | <1.5 | <400 |
| Comparative Preparation Example 3 | 3 | Propylene | About 25% | <1 | <400 |

Note:
both the illustrated gas content and selectivity refer to the average value of detection when the system was operated till the catalyst deactivation.

with the raw gas from the separation tower T-1, then exchanged heat in a fourth heat exchanger E-4 with a low temperature refrigerant, and entered the separation tank D-1, the water produced from the reaction and small amount of organics were separated in the separation tank D-1 from the gaseous alkane and the residual hydrogen, then discharged from the bottom of the separation tank D-1, and delivered to the sewage treatment system; the gaseous alkane containing small amount of hydrogen exited from the top of the separation tank D-1 to recycled to the buffer tank for pre-separation V-1.

The specific operating condition of the above steps were as shown in Table 4, the oxygen contents of the respective stages were detected by an on-line detection and control system for oxygen content (the results were illustrated in Table 4), each of the gas content values shown in Table 4 referred to the detected average value when the system was operated for 500 h.

The catalysts described in Table 4 and a portion of the catalysts illustrated in Table 5 were prepared with the following method: 50 g of $Al_2O_3$ sphere having a dimension of φ2×4 mm was prepared by the extrusion method, and impregnated in 50 ml of KOH solution having a concentration of 5 wt. % for 50 min, then dried in a drying oven at the temperature of 200° C. 0.15 g of $PdCl_2$ was taken and prepared into a solution, the pH of said solution was adjusted to 3, the solution was then poured onto the $Al_2O_3$ carrier, the carrier was subjected to drying at 200° C. for 6 hours, and calcination at 500° C. for 4 hours, and subjected to reducing with $H_2$ at 150° C. for 2 hours, then cooled to room temperature, that is, a deoxygenation catalyst having a Pd content of 0.18 g/100 g $Al_2O_3$ was obtained, and the different deoxygenation catalysts were prepared by adjusting the used amount of $PdCl_2$ or the type of carrier.

TABLE 4

| | | Example 1 | Example 2 | Example 3 | Comparative Example 1 | Comparative Example 2 |
|---|---|---|---|---|---|---|
| Composition of oxygen-containing gas | | 85 vol. % of propene, 15 vol. % of $O_2$ | 40 vol. % of 3-chloro-propene, 60 vol. % of $O_2$ | 80 vol. % of propene, 18 vol.% of $O_2$, and 2 vol. % of methanol | Same as Example 1 | Same as Example 1 |
| Gaseous alkane | Type | Methane | Ethane | Propane | Nitrogen | Carbon dioxide |
| | Volume ratio to $O_2$ in oxygen-containing gas | 14.3 | 18.2 | 19.8 | 14.4 | 13.9 |
| Separation tower | Pressure (MPa) | 1.1 | 0.7 | 1.1 | Same as Example 1 | Same as Example 1 |
| | Temperature (° C.) | 25 | 23 | 28 | Same as Example 1 | Same as Example 1 |
| | $O_2$ content in noncondens-able gas (vol. %) | 6.5 | 5.2 | 4.8 | 6.5 | 6.7 |
| | Gaseous alkane content in noncondens-able gas (vol. %) | 93.2 | 94.7 | 94.9 | 93.4 | 93.1 |
| | Alkene content in noncondens-able gas, vol. % | Propylene, 0.3 | 3-chloro-propene, 0.1 | Propylene, 0.2; methanol, 0.1 | Propylene, 0.1 | Propylene, 0.2 |
| The temperature reached after heating (activation temperature of catalyst, ° C.) | | 50 | 49 | 52 | Same as Example 1 | Same as Example 1 |
| Deoxygen-ation | Catalyst | Pd/ZSM-5 carrier, the amount of Pd is about 0.5 g/100 g carrier | Pd/Al₂O₃ carrier, the amount of Pd is about 0.4 g/100 g carrier | Pd/Al₂O₃ carrier, the amount of Pd is about 0.3 g/100 g carrier | Same as Example 1 | Same as Example 1 |
| | Gas hourly space velocity (h⁻¹) | 3,000 | 4,000 | 2,500 | Same as Example 1 | Same as Example 1 |
| | Temperature (° C.) | 196 | 190 | 188 | Same as Example 1 | Same as Example 1 |
| | Pressure (MPa) | 1.1 | 0.7 | 1.1 | Same as Example 1 | Same as Example 1 |
| Separation tank | Temperature (° C.) | 30 | 25 | 33 | / | / |
| | $O_2$ content at outlet (vol. %) | 0.15 | 0.17 | 0.12 | / | / |

TABLE 4-continued

|  | Example 1 | Example 2 | Example 3 | Comparative Example 1 | Comparative Example 2 |
|---|---|---|---|---|---|
| O$_2$ conversion ratio (%) | 97.7 | 96.7 | 97.5 | / | / |
| H$_2$ content at outlet (vol. %) | 0.11 | 0.14 | 0.15 | / | / |
| Gaseous alkane content at outlet (vol. %) | 99.74 | 99.69 | 99.73 | / | / |
| Carbon deposition amount of the catalyst after operating for 500 h (wt. %) | 7.7 | 8.0 | 8.1 | / | / |
| Stable operation time (h) | Burning and explosion, and temperature runaway did not occur when operating for 500 h | Burning and explosion, and temperature runaway did not occur when operating for 500 h | Burning and explosion, and temperature runaway did not occur when operating for 500 h | Burning and temperature runaway occurred during deoxygenation, the reaction was terminated | Burning and temperature runaway occurred during deoxygenation, the reaction was terminated |

As can be seen from above results, the alkane-assisted light hydrocarbon hydrocatalytic deoxygenation technology in the present application exhibits the technical characteristics such as simple operation, low costs, the deoxygenation can be performed continuously for a long time period, and the operational safety is ensured with high reliability, thus the technology has a widespread application prospect.

Examples 4-6

The oxygen-containing gas was diluted with gaseous alkane, and separated the unsaturated hydrocarbons with C2 or more from the noncondensable gases (gaseous alkane, oxygen) in the separation tower according to the same method of Example 1, the noncondensable gases consisting of the gaseous alkane and oxygen was mixed with hydrogen (the gaseous alkane was used in such an amount that the percentage of gaseous alkane in the total volume of gases in the system of oxidation reaction in each step was as shown in Table 5, and the hydrogen was used in such an amount that a volume ratio of hydrogen to oxygen in the mixed gas was 2.2), the mixed gas was then divided into 4 parts, namely a first part of mixed gas, a second part of mixed gas, a third part of mixed gas and a fourth part of mixed gas, the four parts of mixed gas were subjected to the oxidation reaction according to the following steps:

(a) subjecting the first part of mixed gas to an oxidation reaction in the presence of a first catalyst to obtain a first part of deoxygenated gas;

(b) subjecting the second part of the mixed gas and the first part of deoxygenated gas obtained in step (a) to an oxidation reaction in the presence of a second catalyst to obtain a second part of deoxygenated gas;

(c) subjecting the third part of the mixed gas and the second part of deoxygenated gas obtained in step (b) to an oxidation reaction in the presence of a third catalyst to obtain a third part of deoxygenated gas;

(d) subjecting the fourth part of the mixed gas and the third part of deoxygenated gas obtained in step (c) to an oxidation reaction in the presence of a fourth catalyst to obtain a fourth part of deoxygenated gas;

(e) subjecting the fourth part of deoxygenated gas to an oxidation reaction in the presence of a post-treatment catalyst, to obtain an exit gas.

In each of above steps, the reaction pressure was controlled to be 0.5 MPa, the catalysts in use had the same type of the active ingredient, the supporting amount of the active metal were different, the other operating condition and the evaluation results such as service life of catalyst in each step were shown in Table 5.

TABLE 5

|  |  | Example 4 | Example 5 | Example 6 |
|---|---|---|---|---|
| Composition of oxygen-containing gas |  | 85 vol. % of propene, 15 vol. % of O$_2$ | 40 vol. % of 3-chloropropene, 60 vol. % of O$_2$ | 80 vol. % of propene, 18 vol. % of O$_2$, and 2 vol. % of methanol |
| Gaseous alkane | Type | Methane | Ethane | Propane |
|  | Percentage in the system of oxidation reaction (vol. %) | 93.3 | 95.1 | 97.6 |

TABLE 5-continued

| | | Example 4 | Example 5 | Example 6 |
|---|---|---|---|---|
| (a) | Percentage of the first part of mixed gas | 30% | 35% | 40% |
| | Temperature (° C.) | 60 | 65 | 75 |
| | Hourly space velocity (h⁻¹) | 5500 | 6000 | 6500 |
| | Catalyst | C2 | C2 | C2 |
| (b) | Percentage of the second part of mixed gas | 20% | 35% | 30% |
| | Temperature (° C.) | 80 | 90 | 96 |
| | Hourly space velocity (h⁻¹) | 7000 | 7500 | 8500 |
| | Catalyst | C1 | C1 | C1 |
| (c) | Percentage of the third part of mixed gas | 30% | 25% | 20% |
| | Temperature (° C.) | 120 | 130 | 135 |
| | Hourly space velocity (h⁻¹) | 8000 | 8500 | 9500 |
| | Catalyst | C2 | C1 | C2 |
| (d) | Percentage of the fourth part of mixed gas | 20% | 5% | 10% |
| | Temperature (° C.) | 160 | 180 | 180 |
| | Hourly space velocity (h⁻¹) | 10000 | 10000 | 15000 |
| | Catalyst | C2 | C2 | C1 |
| (e) | Temperature (° C.) | 206 | 210 | 205 |
| | Hourly space velocity (h⁻¹) | 10000 | 10000 | 15000 |
| | O₂ content of exit gas (vol. %) | 0.12 | 0.1 | 0.06 |
| | Catalyst | Pd/Al₂O₃ carrier, the amount of Pd is about 0.1 g/100 g carrier | Pd/Al₂O₃ carrier, the amount of Pd is about 0.2 g/100 g carrier | Pd/Al₂O₃ carrier, the amount of Pd is about 0.2 g/100 g carrier |
| | O₂ conversion ratio (%) | 98.2 | 97.8 | 96.7 |
| | Carbon deposition amount of the catalyst after operating for 500 h (wt. %) | 2.6 | 3.0 | 3.2 |
| | Stable operation time (h) | Burning and explosion, and temperature runaway did not occur when operating for 500 h | Burning and explosion, and temperature runaway did not occur when operating for 500 h | Burning and explosion, and temperature runaway did not occur when operating for 500 h |

Note:
each gas content values as shown refers to the average value of detection when the system is operated for 500 h.

As can be seen from the results of Table 4 and Table 5, an use of the multi-stage oxidation reaction can ensure the deoxygenation effect and reduce the amount of carbon deposition of catalyst in the case of a catalyst having a low precious metal content and a large hourly space velocity, thus the multi-oxidation reaction can be used for further improving the deoxygenation efficiency, the gaseous alkane is used at a low amount and the system running time is long.

Comparative Example 3

The oxygen-containing gas was treated according to the same method as that in Example 4, except that the gaseous alkane was replaced with nitrogen, the results were shown in Table 6.

TABLE 6

| | First catalyst | O₂ content in exit gas (vol. %) | O₂ conversion ratio (%) | Stable operation time (h) |
|---|---|---|---|---|
| Comparative Example 3 | / | 0.13 | 97.4 | Burning and temperature runaway occurred at 90 h, the reaction was terminated |

The above content describes in detail the preferred embodiments of the present invention, but the present invention is not limited thereto. A variety of simple modifications can be made in regard to the technical solutions of the present invention within the scope of the technical concept of the present invention, including a combination of individual technical features in any other suitable manner, such simple modifications and combinations thereof shall also be regarded as the content disclosed by the present invention, each of them falls into the protection scope of the present invention.

The invention claimed is:

1. A method for deoxygenation of an oxygen-containing gas, wherein the oxygen-containing gas comprises unsaturated hydrocarbon, comprising:

removing the unsaturated hydrocarbon from the oxygen-containing gas in presence of a gaseous alkane to obtain a processed oxygen-containing gas further comprising gaseous alkane;

mixing hydrogen with the processed oxygen-containing gas to form a mixed gas; and

carrying out an oxidation reaction in the mixed gas between the oxygen contained in the processed oxygen-containing gas and the hydrogen.

2. The method according to claim 1, wherein a volume ratio of the gaseous alkane to oxygen in the oxygen-containing gas is not lower than 4.

3. The method according to claim 1, wherein the gaseous alkane is 60 vol. % or more of a total volume of the oxygen-containing gas and the gaseous alkane.

4. The method according to claim 1, wherein the gaseous alkane is selected from C1-C4 alkanes.

5. The method according to claim 1, wherein the oxidation reaction is carried out in presence of a catalyst comprising a carrier, an active ingredient, and a coagent supported on the carrier, wherein the active ingredient comprises a precious metal, the coagent comprises an alkali metal, an alkaline earth metal, or both, wherein a percentage of pore volume of pores with pore diameter less than 20 nm in a total pore volume of the catalyst is more than 80% and less than 98%, and a weight ratio of the coagent calculated in terms of metal element in the catalyst to the active ingredient calculated in terms of metal element in the catalyst is more than 10 to less than 100.

6. The method according to claim 5, wherein the coagent comprises the alkali metal and the alkaline earth metal, and a weight ratio of the alkali metal to the alkaline earth metal is 5-10:1; or a weight content of the coagent calculated in terms of metal element in the catalyst ranges from 0.1% to 20%; or a weight content of the active ingredient calculated in terms of metal element in the catalyst ranges from 0.01% to 5%.

7. The method according to claim 1, wherein the oxygen-containing gas comprises 3-99.5 vol. % oxygen and 0.5-99.99 vol. % of the unsaturated hydrocarbon; or the oxygen-containing gas comprises at least one selected from ethylene, ethylene oxide, propylene, propylene oxide, 1-butene, 2-butene, isobutylene, 1,3-butadiene, acetylene, propyne, 1-butyne, 2-butyne, vinyl chloride, 3-chloropropene, 1-chloropropane, 2-chloropropane, and epoxy chloropropane.

8. The method according to claim 1, wherein a volume ratio of hydrogen to oxygen in the processed oxygen-containing gas is within a range of 0.5-5;

and/or a temperature of oxidation reaction is below a light-off temperature for catalytic combustion of gaseous alkane.

9. The method of claim 1, further comprising:

dividing the mixed gas into n parts, n being an integer of 2-20, and subjecting a first part to an nth part of the mixed gas to the oxidation reaction in a sequence of n steps that includes:

step 1: subjecting the first part of mixed gas to an oxidation reaction in the presence of a first gaseous alkane and a first catalyst to obtain a first part of deoxygenated gas;

step 2: subjecting the second part of mixed gas and the first part of deoxygenated gas to an oxidation reaction in presence of a second gaseous alkane and a second catalyst to obtain a second part of deoxygenated gas; and continuing the sequence as needed until step n: subjecting the nth part of mixed gas and the (n-1)th part of deoxygenated gas to an oxidation reaction in presence of an nth gaseous alkane and an nth catalyst to obtain an nth part of deoxygenated gas.

10. The method according to claim 9, wherein:

when n is 13 to 20, a volume concentration of oxygen in the oxidation reaction in each of step 13 to step 20 is larger than or equal to 15 vol. %; or when n is 9 to 12, a volume concentration of oxygen content e in the oxidation reaction in each of step 9 to step 12 is less than 15 vol. % and larger than or equal to 10 vol. %; or when n is 6 to 8, a volume concentration of oxygen in the oxidation reaction in each of step 6 to step 8 is less than 10 vol. % and larger than or equal to 6 vol. %; or when n is 2 to 5, a volume concentration of oxygen in the oxidation reaction in each of step 2 to step 5 is less than 6 vol. %.

11. The method according to claim 9, wherein a temperature of the oxidation reaction in each of the n steps ranges from 30-380° C., a pressure ranges from 0.3-5 MPa, and a gas hourly space velocity in terms of total volume ranges from 500-45,000 $h^{-1}$.

12. The method according to claim 1, wherein an oxygen content in a residual gas after the oxidation reaction is 1.5 vol. % or less.

13. The method according to claim 1, wherein a residual gas after the oxidation is recycled as the gaseous alkane.

14. The method according to claim 1, wherein a volume ratio of the gaseous alkane to oxygen in the oxygen-containing gas is greater than 5.

15. The method according to claim 1, wherein the gaseous alkane comprises at least one of methane, ethane and propane.

16. The method according to claim 1, wherein a volume ratio of hydrogen to oxygen in the processed oxygen-containing gas is within a range of 1-3.

17. The method according to claim 12, wherein the oxygen content in the residual gas is 0.5 vol. % or less.

* * * * *